United States Patent [19]

Montavon et al.

[11] 4,292,428
[45] * Sep. 29, 1981

[54] CEPHALOSPORIN DERIVATIVES

[75] Inventors: Marc Montavon; Roland Reiner, both of Basel, Switzerland

[73] Assignee: Hoffmann-La Roche Inc., Nutley, N.J.

[*] Notice: The portion of the term of this patent subsequent to Dec. 11, 1996, has been disclaimed.

[21] Appl. No.: 51,669

[22] Filed: Jun. 25, 1979

[30] Foreign Application Priority Data

Jul. 19, 1978 [CH] Switzerland .................. 7786/78

[51] Int. Cl.³ .......................................... C07D 501/56
[52] U.S. Cl. .......................................... 544/27; 544/26
[58] Field of Search .................................. 544/26, 27

[56] References Cited
U.S. PATENT DOCUMENTS

| | | | |
|---|---|---|---|
| 4,074,047 | 2/1978 | Foxton et al. | 544/27 |
| 4,091,211 | 5/1978 | Montavon et al. | 544/27 |
| 4,178,443 | 12/1979 | Montavon et al. | 544/26 |

*Primary Examiner*—Paul M. Coughlan, Jr.
*Attorney, Agent, or Firm*—Jon S. Saxe; Bernard S. Leon; Frank P. Hoffman

[57] ABSTRACT

There is presented cephalosporin derivatives which are the readily hydrolysable esters and ethers of compounds of the general formula

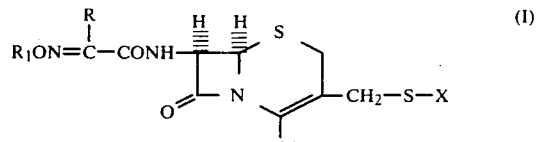

wherein R represents furyl, thienyl or phenyl optionally substituted by halogen, hydroxy, lower alkoxy or lower alkyl, $R_1$ represents lower alkyl or aminocarbonylmethyl and X represents a group of the formula

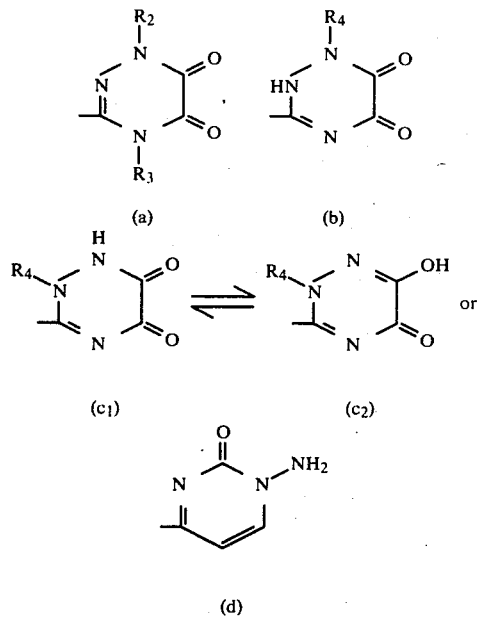

in which one of the two symbols $R_2$ and $R_3$ represents hydrogen and the other represents lower alkyl and $R_4$ represents lower alkyl, as well as salts of said esters and ethers and hydrates of said esters, ethers and salts.

9 Claims, No Drawings

CEPHALOSPORIN DERIVATIVES

DESCRIPTION OF THE INVENTION

The present invention is concerned with cephalosporin derivatives, a process for the manufacture thereof and pharmaceutical preparations containing same.

The cephalosporin derivatives provided by the present invention are readily hydrolysable esters and ethers of compounds of the general formula

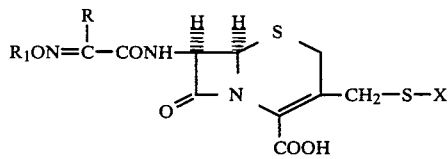

wherein R represents furyl, thienyl or phenyl optionally substituted by halogen, hydroxy, lower alkoxy or lower alkyl, $R_1$ represents lower alkyl or aminocarbonylmethyl and X represents a group of the formula

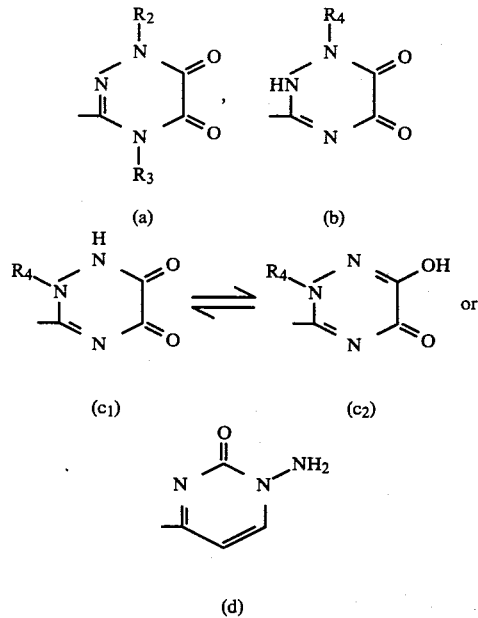

in which one of the two symbols $R_2$ and $R_3$ represents hydrogen and the other represents lower alkyl and $R_4$ represents lower alkyl,
as well as salts of said esters and ethers and hydrates of said esters, ether and salts.

As readily hydrolysable esters of the compounds of formula I there are to be understood compounds of formula I in which the carboxy group is present in the form of a readily hydrolysable ester group. Examples of such esters are the lower alkanoyloxyalkyl esters (e.g. the acetoxymethyl, pivaloyloxymethyl, 1-acetoxyethyl and 1-pivaloyloxyethyl ester), the lower alkoxycarbonyloxyalkyl esters (e.g. the methoxycarbonyloxymethyl, 1-ethoxycarbonyloxyethyl and 1-isopropoxycarbonyloxyethyl ester), the lactonyl esters (e.g. the phthalidyl and thiophthalidyl ester), the lower alkoxymethyl esters (e.g. the methoxy-methyl ester) and the lower alkanoylaminomethyl esters (e.g. the acetamidomethyl ester). Other esters (e.g. the benzyl and cyanomethyl ester) can also be used.

As readily hydrolysable ethers of the compounds of formula I there are to be understood compounds of formula I wherein X represents a group of formula ($c_2$) in which the enolic OH group is present in the form of a readily hydrolysable ether group. Possible ether groups are the same groups which have already been mentioned earlier in connection with the readily hydrolysable ester groups. Examples of such ethers are thus, for example, the lower alkanoyloxyalkyl ethers (e.g. the acetoxymethyl, pivaloyloxymethyl, 1-acetoxyethyl and 1-pivaloyloxyethyl ether), the lower alkoxycarbonyloxyalkyl ethers (e.g. the methoxycarbonyloxymethyl, 1-ethoxycarbonyloxyethyl and 1-isopropoxycarbonyloxyethyl ether), the lactonyl ethers (e.g. the phthalidyl and thiophthalidyl ether), the lower alkoxymethyl ethers (e.g. the methoxymethyl ether) and the lower alkanoylaminomethyl ethers (e.g. the acetamidomethyl ether).

Examples of salts of the esters or ethers provided by the present invention are salts with bases; for example, alkali metal salts such as the sodium salt and the potassium salt, the ammonium salt, alkaline earth metal salts such as the calcium salt, salts with organic bases such as salts with amines (e.g. salts with N-ethylpiperidine, procaine, dibenzylamine, N,N'-dibenzylethylethylenediamine, alkylamines or dialkylamines) and salts with amino acids (e.g. salts with arginine or lysine). For the formation of salts with bases it is essential that the compound of formula I contains a free carboxy group and/or a free enolic OH group.

The compounds of formula I also form addition salts with organic or inorganic acids. Examples of such salts are hydrohalides (e.g. hydrochlorides, hydrobromides and hydroiodides), other mineral acid salts such as sulphates, nitrates, phosphates and the like, alkylsulphonates and monoarylsulphonates such as ethanesulphonates, toluenesulphonates, benzenesulphonates and the like and other organic acid salts such as acetates, tartrates, maleates, citrates, benzoates, salicylates, ascorbates and the like.

The esters and ethers of the compounds of formula I and the salts of said esters and ethers can be hydrated. The hydration can be effected in the course of the manufacturing process or can occur gradually as a result of the hygroscopic properties of an initially anhydrous product.

The aforementioned lower alkyl groups are either straight-chain or branched-chain and can contain up to 7 carbon atoms (e.g. methyl, ethyl, n-propyl, isopropyl, n-pentyl and n-heptyl). The lower alkoxy groups have an analogous significance. The halogen atom is fluorine, chlorine, bromine or iodine with chlorine and bromine being preferred.

Preferred groups denoted by R are furyl, thienyl and phenyl, especially furyl. $R_1$ preferably represents methyl. X preferably represents a group of formula (d), a group of formula (a) in which one of the two symbols $R_2$ and $R_3$ represents hydrogen and the other represents methyl or a group of formula (b), ($c_1$) or ($c_2$) in which $R_4$ represents methyl. Especially preferred groups denoted by X are the 1,2,5,6-tetrahydro-2-methyl-5,6-dioxo-as-triazin-3-yl group, the corresponding tautomeric form thereof, i.e. the 2,5-dihydro-6-hydroxy-2-methyl-5-oxo-as-triazin-3-yl group (which, as mentioned earlier, is etherified on the hydroxy group), and the 1,4,5,6-tetrahydro-4-methyl-5,6-dioxo-as-triazin-3-yl group.

The esters and ethers of the compounds of formula I as well as salts and hydrates thereof can exist in the syn-isomeric form

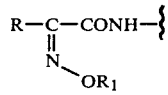

or in the anti-isomeric form

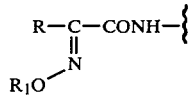

or as mixtures of these two forms. The syn-isomeric form is preferred as are mixtures in which the syn-isomeric form predominates.

Preferred cephalosporin derivatives provided by the present invention are:

Methylene-(6R,7R)-7-[2-(2-furyl)-2-(methoxyimino)-acetamido]-8-oxo-3-[[(1,4,5,6-tetrahydro-4-methyl-5,6-dioxo-as-triazin-3-yl)thio]methyl]-5-thia-1-azabicyclo-[4.2.0]oct-2-ene-2-carboxylate pivalate (Z-isomer), methylene-(6R,7R)-3-{[[2,5-dihydro-2-methyl-5-oxo-6-[(pivaloyloxy)methoxy]-as-triazin-3-yl]thio]methyl}-7-[2-(2-furyl)-2-(methoxyimino)acetamido]-8-oxo-5-thia-1-aza-bicyclo[4.2.0]oct-2-ene-2-carboxylate pivalate (Z-isomer), and salts thereof as well as the corresponding hydrates.

According to the process provided by the present invention, the cephalosporin derivatives aforesaid are manufactured by (a) subjecting a carboxylic acid or enol of formula I to a corresponding esterification or etherification, or (b) reacting a readily hydrolysable ester or ether of a carboxylic acid of the general formula

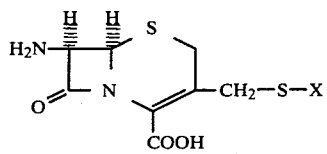

, wherein X has the significance given earlier, with an acid of the general formula

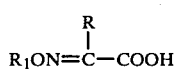

, wherein R and $R_1$ have the significance given earlier, or with a reactive functional derivative of this acid, or (c) for the manufacture of a readily hydrolysable ether of a compound of formula I, reacting a carboxylic acid of the general formula

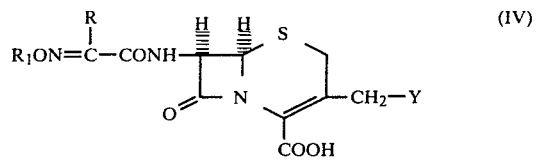

, wherein R and $R_1$ have the significance given earlier and Y represents a leaving group,
with a thiol of the general formula

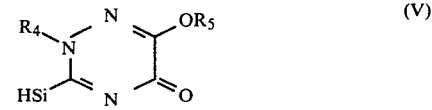

, wherein $R_4$ has the significance given earlier and $R_5$ represents a readily cleavable ether group,
and, if desired, converting the product obtained into a salt or hydrate or a hydrate of such a salt.

In order to manufacture a readily hydrolysable ester of a carboxylic acid of formula I in accordance with embodiment (a) of the process provided by the present invention, a carboxylic acid of formula I is preferably reacted with a corresponding halide, preferably an iodide, containing the desired ester group. The reaction can be accelerated with the aid of a base such as an alkali metal hydroxide or carbonate or an organic amine (e.g. triethylamine). If the group of formula ($c_2$) with its enolic function is present, this is etherified with the formation of a corresponding readily hydrolysable ether. In this case there is preferably used an excess of the corresponding halide. The esterification/etherification is preferably carried out in an inert organic solvent such as dimethylacetamide, hexamethylphosphoric acid triamide, dimethyl sulphoxide or, especially, dimethylformamide. The reaction is preferably carried out at a temperature in the range of about 0°–40° C.

The readily hydrolysable esters or ethers of the carboxylic acids of formula II used as starting materials in embodiment (b) of the process provided by the present invention are prepared in an entirely analogous manner to that described earlier in connection with embodiment (a).

Examples of reactive functional derivatives of acids of formula III include halides (i.e. chlorides, bromides and fluorides), azides, anhydrides, especially mixed anhydrides with strong acids, reactive esters (e.g. N-hydroxysuccinimide esters) and amides (e.g. imidazolides).

The reaction of a readily hydrolysable ester or ether of a carboxylic acid of formula II with an acid of formula III or a reactive functional derivative thereof in accordance with embodiment (b) can be carried out in a manner known per se. Thus, for example, a free acid of formula III can be reacted with one of the aforementioned esters or ethers in the presence of a carbodiimide (e.g. dicyclohexylcarbodiimide) in an inert solvent (e.g. ethyl acetate, acetonitrile, dioxan, chloroform, methylene chloride, benzene or dimethylformamide). Oxazolium salts (e.g. N-ethyl-5-phenyl-isoxazolium-3'-sulphonate) can be used in place of carbodiimides.

According to a further aspect of embodiment (b), an acid halide, preferably the chloride, of an acid of formula III is used as the starting material. The reaction is preferably carried out in the presence of an acid-binding agent; for example, in the presence of aqueous alkali, preferably sodium hydroxide, or in the presence of an alkali metal carbonate such as potassium carbonate, or in the presence of a lower-alkylated amine such as triethylamine. Water is preferably used as the solvent, although the reaction can also be carried out in an aprotic organic solvent such as, for example, dimethylformamide, dimethyl sulphoxide or hexamethylphosphoric acid triamide.

The reaction of a readily hydrolysable ester or ether of a carboxylic acid of formula II with an acid of formula III or a reactive functional derivative thereof can be carried out conveniently at a temperature between about −40° C. and room temperature, for example at about 0°–10° C.

Examples of leaving groups denoted by Y in carboxylic acids of formula IV include halogen atoms (e.g. chlorine, bromine or iodine), acyloxy groups (e.g. lower alkanoyl groups such as acetoxy), lower alkylsulphonyloxy or arylsulphonyloxy groups (e.g. mesyloxy or tosyloxy) and the azido group.

The reaction of a carboxylic acid of formula IV with a thiol of formula V in accordance with embodiment (c) of the process provided by the present invention can be carried out in a manner known per se; for example, at a temperature between about 40° C. and 80° C., conveniently at about 60° C., in a polar solvent such as an alcohol (e.g. a lower alkanol such as ethanol, propanol and the like), dimethylformamide or dimethyl sulphoxide, but preferably in water or in a buffer solution having a pH of about 6 to 7, preferably 6.5.

The readily hydrolysable esters and ethers of the carboxylic acids of formula II used as starting materials in embodiment (b) of the present process can be prepared by reacting a readily hydrolysable ester or ether of a compound of the general formula

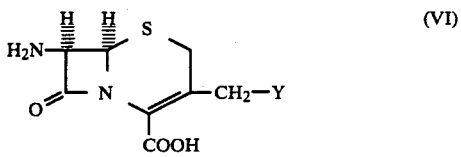

(VI)

, wherein Y represents a leaving group,
with a thiol of formula V. The reaction can be carried out under the same conditions as described earlier in connection with the reaction of a carboxylic acid of formula IV with a thiol of formula V.

A syn/anti mixture of a readily hydrolysable ester or ether of a compound of formula I which may be obtained can be separated into the corresponding syn and anti forms in the customary manner; for example, by recrystallisation or by chromatographic methods using a suitable solvent or solvent mixture.

The cephalosporin derivatives provided by the present invention have antibiotic, especially bactericidal, activity. They have a broad spectrum of activity against gram-positive and gram-negative microorganisms, including β-lactamase-forming Staphylococci and various β-lactamase-forming gram-negative bacteria such as, for example, Haemophilus influenzae, *Escherichia coli*, Proteus and Klebsiella species.

The cephalosporin derivatives provided by the present invention can be used for the treatment and prophylaxis of infectious diseases. In the case of adults a daily dosage of about 1 g to about 4 g may be administered.

The present cephalosporin derivatives can be administered not only orally but also parenterally.

In order to demonstrate the antimicrobial activity of the cephalosporin derivatives provided by the present invention, following representative derivatives were tested:

Derivative A:
Methylene-(6R,7R)-7-[2(2-furyl)-2-(methoxyimino)-acetamido]-8-oxo-3-]][(1,4,5,6-tetrahydro-4-methyl-5,6-dioxo-as-triazin-3-yl)thio]methyl]-5-thia-1-azabicyclo[4.2.0]oct-2-ene-2-carboxylate pivalate (Z-isomer).

Derivative B:
Methylene-(6R,7R)-3-{[[2,5-dihydro-2-methyl-5-oxo-6-[(pivaloyloxy)methoxy]-as-triazin-3-yl]thio]methyl}-7-[2-(2-furyl)-2-(methoxyimino)acetamido]-8-oxo-5-thia-1-azabicyclo[4.2.0]oct-2-ene-2-carboxylate pivalate (Z-isomer).

Activity in vivo:
Groups of 5 mice are infected intraperitoneally with an aqueous suspension of Escherichia coli. The derivative to be tested is administered orally or subcutaneously 1, 2.5 and 4 hours after the infection. The number of surviving mice is determined on the 4th day. Various dosages of the derivative are administered and the dosage at which 50% of the mice survive ($CD_{50}$, mg/kg) is determined by interpolation.

| Test derivative | A (oral) | A (subcutaneous) | B (oral) | B (subcutaneous) |
|---|---|---|---|---|
| $CD_{50}$, mg/kg | 0.05 | 0.02 | 0.03 | 0.02 |

| | Toxicity: (mice, 24 hour value) | |
|---|---|---|
| Test derivative | A | B |
| $LD_{50}$, mg/kg p.o. | 2500–5000 | 1250–2500 |

The cephalosporin derivatives provided by the present invention can be used as medicaments, for example in the form of pharmaceutical preparations which contain them in association with a compatible pharmaceutical carrier material. This carrier material can be an organic or inorganic inert carrier material suitable for enteral or parenteral administration such as, for example, water, gelatin, gum arabic, lactose, starch, magnesium stearate, talc, vegetable oils, polyalkyleneglycols, petroleum jelly etc. The pharmaceutical preparations can be made up in a solid form (e.g. as tablets, dragées, suppositories or capsules) or in a liquid form (e.g. as solutions, suspensions or emulsions). The pharmaceutical preparations may be sterilised and/or may contain adjuvants such as preserving, stabilising, wetting or emulsifying agents, salts for varying the osmotic pressure, anaesthetics or buffers. The pharmaceutical preparations can also contain other therapeutically valuable substances.

The following Examples illustrate the process provided by the present invention:

EXAMPLE 1

Methylene-(6R,7R)-7-[2-(2-furyl)-2-(methoxyimino)-acetamido]-8-oxo-3-[[(1,4,5,6-tetrahydro-4-methyl-5,6-dioxo-as-triazin-3-yl)thio]methyl]-5-thia-1-azabicyclo-[4.2.0]oct-2-ene-2-carboxylate pivalate (Z-isomer).

5.2 g of (7R)-7-[2-(2-furyl)-2-(methoxyimino)-acetamido]-3-[[(1,4,5,6-tetrahydro-4-methyl-5,6-dioxoas-triazin-3-yl)thio]methyl]-3-cephem-4-carboxylic acid in 30 ml of dimethylformamide are treated at 0° C. with 2.8 ml of triethylamine and 5.3 g of iodomethyl pivalate and the mixture is stirred for 10 minutes while gassing with nitrogen. The mixture is diluted with 250 ml of ethyl acetate and extracted with 5% aqueous sodium bicarbonate solution and water. The ethyl acetate solution is dried over magnesium sulphate and evaporated. The oil obtained is dissolved in a small amount of ethyl acetate and precipitated with low-boiling petroleum ether. The precipitate is filtered off, dissolved in ethyl acetate and chromatographed with ethyl acetate over silica gel. The uniform fractions are evaporated and the oil obtained is precipitated from ethyl acetate with n-hexane. After suction filtration and drying, the pure title substance is obtained:

$[\alpha]_D^{25} = -66.1°$ (c=1 in ethyl acetate).

NMR: Spectrum in agreement with the structure.

The substance contains 0.3 mol of n-hexane.

Calculated: C: 48.35%; H: 4.84%; N: 12.76%; S: 9.74%. Found: C: 48.17%; H: 5.05%; N: 12.39%; S: 9.60%.

EXAMPLE 2

Methylene-(6R,7R)-3-{[[2,5-dihydro-2-methyl-5-oxo-6-[(pivaloyloxy)methoxy]-as-triazin-3-yl]thio]methyl}-7-[2-furyl)-2-(methoxyimino)acetamido]-8-oxo-5-thia-1-aza-bicyclo[4.2.0]oct-2-ene-2-carboxylate pivalate (Z-isomer).

5.7 g of (Z)-(7R)-[2-(2-furyl)-2-(methoxyimino)-acetamido]-3-[[(2,5-dihydro-6-hydroxy-2-methyl-5-oxo-as-triazin-3-yl)thio]methyl]-3-cephem-4-carboxylic acid disodium salt are cooled to 0° C. in 30 ml of dimethylformamide, treated while stirring with 2.8 ml of triethylamine and thereafter with 5.3 g of iodomethyl pivalate and the mixture is then stirred for 10 minutes under nitrogen. After dilution with 250 ml of ethyl acetate, the mixture is washed with 5% aqueous sodium bicarbonate solution and water, dried over magnesium sulphate and evaporated at 12 Torr. The oil obtained is dissolved in a small amount of ethyl acetate and precipitated with low-boiling petroleum ether. The precipitate is filtered off, dissolved in ethyl acetate and chromatographed over silica gel with ethyl acetate. The title substance is obtained from the uniform fractions after evaporation and precipitation from ethyl acetate with low-boiling petroleum ether:

$[\alpha]_D^{25} = -200.2°$ (c=1 in ethyl acetate).

Melting point: from 105° C.

NMR: Spectrum in agreement with the structure.

Calculated: C: 49.59%; H: 5.10%; N: 11.19%; S: 8.54%. Found: C: 50.08%; H: 5.22%; N: 11.00%; S: 8.41%.

The following Examples illustrate pharmaceutical preparations containing the cephalosporin derivatives provided by the present invention:

EXAMPLE A

Production of dry ampoules for parenteral administration:

A lyophilisate of 500 mg of methylene-(6R,7R)-7-[2-(2-furyl)-2-(methoxyimino)acetamido]-8-oxo-3-[[(1,4,5,6-tetrahydro-4-methyl-5,6-dioxo-as triazin-3-yl)thio]-methyl]-5-thia-1-azabicyclo[4.2.0]oct-2-ene-2-carboxylate pivalate (Z-isomer) is prepared in the customary manner and filled into an ampoule.

EXAMPLE B

Interlocking gelatine capsules containing the following ingredients are produced in the customer manner:

| | |
|---|---|
| Methylene-(6R,7R)-3-{[[2,5-dihydro-2-methyl-5-oxo-6-[(pivaloyloxy)methoxy]-as-triazin-3-yl}thio]methyl]-7-[2-(2-furyl)-2-methoxyimino)acetamido]-8-oxo-5-thia-1-azabicyclo[4.2.0]oct-2-ene-2-carboxylate pivalate (Z-isomer) | 500 mg |
| Luviskol (water-soluble polyvinylpyrrolidone) | 20 mg |
| Mannitol | 20 mg |
| Talc | 15 mg |
| Magnesium stearate | 2 mg |
| | 557 mg |

What is claimed:

1. Readily hydrolysable esters selected from the group consisting of acetoxymethyl, pivaloyloxymethyl, 1-acetoxyethyl, 1-pivaloyloxyethyl, methoxycarbonyloxymethyl, 1-ethoxycarbonyloxyethyl, 1-isopropoxycarbonyloxyethyl, phthalidyl, thiophthalidyl, methoxymethyl, acetamidomethyl, benzyl and cyanomethyl esters and readily hydrolysable ethers selected from the group consisting of the acetoxymethyl, pivaloyloxymethyl, 1-acetoxyethyl, 1-pivaloyloxyethyl, methoxycarbonylmethyl, 1-ethoxycarbonyloxyethyl, 1-isopropoxycarbonyloxyethyl, phthalidyl, thiophthalidyl, methoxymethyl and acetamidomethyl ethers of compounds of the formula

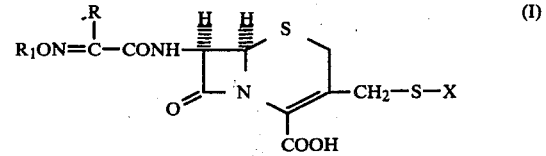

wherein R represents furyl, thienyl, phenyl or phenyl mono-substituted by halo, hydroxy, lower alkoxy or lower alkyl, $R_1$ represents lower alkyl or aminocarbonylmethyl and X represents a group of the formula

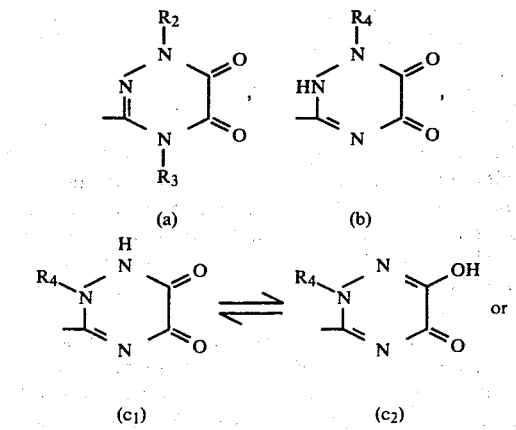

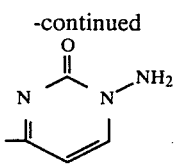

(d)

in which one of the two symbols $R_2$ and $R_3$ represents hydrogen and the other represents lower alkyl and $R_4$ represents lower alkyl, and salts with pharmaceutically acceptable bases or acids of said esters and ethers and hydrates of said esters, ethers and salts.

2. The esters and ethers of claim 1 wherein the esters and ethers are pivaloyloxymethyl esters or ethers.

3. The esters and ethers of claim 1 wherein R represents furyl.

4. The esters and ethers of claim 1 wherein $R_1$ represents methyl.

5. The ester and ethers of claim 1 wherein X represents a group of formula (d), a group of formula (a) in which one of the two symbols $R_2$ and $R_3$ represents hydrogen and the other represents methyl, a group of formula (b) in which $R_4$ represents methyl or a group of formula (c₁) or (c₂) in which $R_4$ represents methyl.

6. The esters and ethers of claim 5, wherein X represents the 1,2,5,6-tetrahydro-2-methyl- 5,6-dioxo-as-triazin-3-yl or 2,5-dihydro-6-hydroxy-2-methyl-5-oxo-as-triazin-3-yl group.

7. The esters of claim 5, wherein X represents the 1,4,5,6-tetrahydro-4-methyl-5,6-dioxo-as-triazin-3-yl group.

8. The compound: methylene-6R,7R)-3-{-[[2,5-dihydro-2-methyl-oxo-6-[(pivaloyloxy)methoxy]-as-triazin-3-yl]thio]methyl}-7-[2-(2-furyl)-2-(methoxyimino)acetamido]-8-oxo-5-thia-1-azabicyclo[4.2.0]oct-2-ene-2-carboxylate pivalate (Z-isomer), as well as salts of said compound and hydrates of said compound and salts.

9. The compound: methylene-(6R,7R)-[2-(2-furyl)-2-(methoxyimino)-acetamido]-8-oxo-3-[[(1,4,5,6-tetrahydro-4-methyl-5,6-dioxo-as-triazin-3-yl)thio]methyl]-5-thia-1-azabicyclo-[4.2.0]oct-2-ene-2-carboxylate pivalate (Z-isomer), as well as salts of said compound and hydrates of said compound and salts.

* * * * *